(12) United States Patent
Biederman et al.

(10) Patent No.: US 12,251,187 B1
(45) Date of Patent: *Mar. 18, 2025

(54) NFC BEACONS FOR BIDIRECTIONAL COMMUNICATION BETWEEN AN ELECTROCHEMICAL SENSOR AND A READER DEVICE

(71) Applicants: Verily Life Sciences LLC, South San Francisco, CA (US); Dexcom, Inc., San Diego, CA (US)

(72) Inventors: William James Biederman, Fox Island, WA (US); Robert Francis Wiser, San Francisco, CA (US); Brian Otis, Saratoga, CA (US)

(73) Assignees: Dexcom, Inc., San Diego, CA (US); Verily Life Sciences LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/895,578

(22) Filed: Aug. 25, 2022

Related U.S. Application Data

(63) Continuation of application No. 15/367,311, filed on Dec. 2, 2016, now Pat. No. 11,457,809.

(Continued)

(51) Int. Cl.
*H04W 12/02* (2009.01)
*A61B 5/00* (2006.01)
(Continued)

(52) U.S. Cl.
CPC .......... *A61B 5/002* (2013.01); *A61B 5/14532* (2013.01); *A61B 5/1495* (2013.01);
(Continued)

(58) Field of Classification Search
CPC ....... H04W 4/80; H04W 12/02; H04W 12/04; H04W 48/10
See application file for complete search history.

(56) References Cited

U.S. PATENT DOCUMENTS 3,872,455 A * 3/1975 Fuller .................... G01K 1/024
340/870.18
3,949,388 A * 4/1976 Fuller .................. A61B 5/0008
128/903

(Continued)

OTHER PUBLICATIONS

U.S. Appl. No. 15/367,311, Final Office Action, Mailed on Feb. 21, 2019, 10 pages.

(Continued)

*Primary Examiner* — David Garcia Cervetti
(74) *Attorney, Agent, or Firm* — Patterson + Sheridan, LLP

(57) ABSTRACT

The present disclosure is related to a sensing device. The sensing device includes a sensor, a memory, a processor, and two radio units. A first radio unit of the two radio units is configured for bidirectional communication with an external device using a first radio communication protocol. The bidirectional communication comprises receiving configuration data from the external device via a first radio signal from the external device. The second radio unit of the two radio units is configured for unidirectional communication with the external device using a second radio communication protocol. The unidirectional communication comprises the second radio unit transmitting a second radio signal to the external device. The second radio signal communicates data including one or more measurements obtained by the sensor.

20 Claims, 8 Drawing Sheets

Related U.S. Application Data

(60) Provisional application No. 62/264,403, filed on Dec. 8, 2015.

(51) Int. Cl.
  *A61B 5/145* (2006.01)
  *A61B 5/1495* (2006.01)
  *H04B 5/72* (2024.01)
  *H04W 4/80* (2018.01)
  *H04W 12/04* (2021.01)
  *H04W 48/10* (2009.01)

(52) U.S. Cl.
  CPC .......... *A61B 5/6801* (2013.01); *A61B 5/6847* (2013.01); *H04B 5/72* (2024.01); *H04W 4/80* (2018.02); *H04W 12/02* (2013.01); *H04W 12/04* (2013.01); *H04W 48/10* (2013.01)

(56) References Cited

U.S. PATENT DOCUMENTS

| | | | | |
|---|---|---|---|---|
| 4,803,886 A * | 2/1989 | May | ................ | G01L 5/102 73/773 |
| 5,324,315 A * | 6/1994 | Grevious | ............ | A61N 1/3727 128/903 |
| 5,392,454 A * | 2/1995 | Kowal | ................ | H04M 1/727 455/500 |
| 5,662,691 A * | 9/1997 | Behan | ................ | A61N 1/37211 607/32 |
| 5,904,708 A * | 5/1999 | Goedeke | ............ | A61B 5/02156 607/18 |
| 6,167,310 A * | 12/2000 | Grevious | ........... | A61N 1/37252 607/32 |
| 6,505,072 B1 * | 1/2003 | Linder | ............... | A61N 1/37211 128/903 |
| 6,535,766 B1 * | 3/2003 | Thompson | ......... | A61N 1/37229 607/32 |
| 6,766,141 B1 * | 7/2004 | Briles | ...................... | H04B 1/38 340/855.8 |
| 6,944,767 B1 | 9/2005 | Judson | | |
| 7,047,076 B1 * | 5/2006 | Li | ...................... | A61N 1/37229 343/718 |
| 7,801,828 B2 * | 9/2010 | Candella | .................. | G07C 9/38 705/40 |
| 8,214,043 B2 | 7/2012 | Matos | | |
| 9,152,775 B1 * | 10/2015 | Kronrod | ................ | G06F 21/31 |
| 9,277,402 B2 * | 3/2016 | Husted | ................ | H04L 63/068 |
| 9,406,067 B1 * | 8/2016 | Robinson | ............ | G06Q 20/4016 |
| 9,516,053 B1 * | 12/2016 | Muddu | ................ | G06F 16/9024 |
| 9,626,315 B2 * | 4/2017 | DeHennis | ............. | G01N 33/50 |
| 9,636,456 B2 * | 5/2017 | Talbot | ............... | A61M 5/14244 |
| 9,699,196 B1 * | 7/2017 | Kolman | ................ | G06F 16/9024 |
| 9,785,401 B2 * | 10/2017 | Yuen | ................ | G06F 16/9024 |
| 9,786,294 B1 * | 10/2017 | Bezos | ...................... | G06F 3/165 |
| 9,870,630 B2 * | 1/2018 | Patil | ........................ | G06Q 10/00 |
| 10,021,087 B2 | 7/2018 | Karimzadeh et al. | | |
| 10,252,063 B2 * | 4/2019 | Min | ...................... | A61B 5/686 |
| 10,579,823 B2 * | 3/2020 | Eigner | ................ | G06F 21/6254 |
| 10,671,752 B1 * | 6/2020 | Misra | ................ | G06Q 50/265 |
| 10,673,880 B1 * | 6/2020 | Pratt | .................... | H04L 63/1425 |
| 10,888,703 B2 * | 1/2021 | Olson | ..................... | H02J 50/90 |
| 11,122,038 B1 * | 9/2021 | Schuster | ............... | H04W 12/06 |
| 11,457,809 B1 | 10/2022 | Biederman et al. | | |
| 11,783,272 B2 * | 10/2023 | Olenoski | ................ | G06Q 10/10 705/330 |
| 2002/0045920 A1 * | 4/2002 | Thompson | ......... | A61N 1/37229 607/60 |
| 2002/0138009 A1 * | 9/2002 | Brockway | ............ | A61B 5/0028 600/500 |
| 2002/0147388 A1 * | 10/2002 | Mass | ................ | A61N 1/37223 600/300 |
| 2002/0147819 A1 * | 10/2002 | Miyakoshi | ............ | H04L 9/40 709/228 |
| 2003/0114769 A1 * | 6/2003 | Loeb | .................... | A61B 5/0031 600/513 |
| 2003/0149459 A1 * | 8/2003 | Von Arx | ............ | A61N 1/37276 607/60 |
| 2003/0158584 A1 * | 8/2003 | Cates | ..................... | A61B 5/076 607/2 |
| 2003/0216682 A1 * | 11/2003 | Junker | ............... | A61M 5/14276 604/246 |
| 2004/0106967 A1 * | 6/2004 | Von Arx | ............ | A61N 1/37229 607/60 |
| 2004/0147969 A1 * | 7/2004 | Mann | ................. | A61B 5/02108 607/17 |
| 2004/0260363 A1 | 12/2004 | Arx et al. | | |
| 2005/0027175 A1 * | 2/2005 | Yang | ................. | A61B 5/14532 600/364 |
| 2005/0104457 A1 * | 5/2005 | Jordan | ...................... | A61F 2/00 310/36 |
| 2005/0136385 A1 * | 6/2005 | Mann | ...................... | A61N 1/025 434/320 |
| 2005/0204134 A1 * | 9/2005 | Von Arx | ............... | H04L 9/0891 713/168 |
| 2005/0245995 A1 * | 11/2005 | Diebold | ............. | A61N 1/37229 607/60 |
| 2005/0246278 A1 * | 11/2005 | Gerber | .................. | G06Q 20/40 705/44 |
| 2005/0258865 A1 * | 11/2005 | Behrendt | ................ | H04L 25/22 326/82 |
| 2006/0038677 A1 * | 2/2006 | Diener | .................. | H04W 12/64 340/540 |
| 2006/0079793 A1 * | 4/2006 | Mann | .................... | A61B 5/4839 607/17 |
| 2006/0080525 A1 * | 4/2006 | Ritter | ...................... | G06F 21/32 713/155 |
| 2006/0122863 A1 * | 6/2006 | Gottesman | ............. | G16H 10/60 705/2 |
| 2006/0122864 A1 * | 6/2006 | Gottesman | ............. | G16H 20/17 600/300 |
| 2006/0148402 A1 * | 7/2006 | Hagiwara | ............. | H04L 9/3226 455/411 |
| 2006/0149324 A1 * | 7/2006 | Mann | ................. | A61N 1/37254 607/9 |
| 2006/0149330 A1 * | 7/2006 | Mann | ................. | A61N 1/37229 607/34 |
| 2006/0159074 A1 * | 7/2006 | Diebold | ............. | H04W 48/18 370/328 |
| 2006/0224326 A1 * | 10/2006 | St. Ores | ................ | G16H 40/67 702/19 |
| 2006/0224421 A1 * | 10/2006 | St. Ores | ................ | G16H 10/20 705/4 |
| 2006/0224901 A1 * | 10/2006 | Lowe | ................... | H04L 63/0492 713/153 |
| 2007/0083246 A1 * | 4/2007 | Mazar | ..................... | H04W 4/80 128/903 |
| 2007/0092114 A1 * | 4/2007 | Ritter | ...................... | G06F 21/32 382/115 |
| 2007/0255116 A1 * | 11/2007 | Mehta | ..................... | G16H 40/67 600/300 |
| 2007/0258395 A1 * | 11/2007 | Jollota | .................. | H04W 72/23 455/67.11 |
| 2007/0293774 A1 * | 12/2007 | Acquista | ................ | A61B 5/282 600/509 |
| 2008/0092638 A1 * | 4/2008 | Brenneman | ............ | G16H 10/40 73/61.41 |
| 2008/0103555 A1 | 5/2008 | Dicks et al. | | |
| 2008/0217411 A1 * | 9/2008 | Ledwith | ............. | G06K 17/0022 235/472.02 |
| 2008/0243088 A1 | 10/2008 | Evans | | |
| 2008/0244717 A1 * | 10/2008 | Jelatis | ............... | A61N 1/37254 726/5 |
| 2008/0287144 A1 * | 11/2008 | Sabata | .................... | H04L 67/12 455/456.6 |
| 2008/0314969 A1 * | 12/2008 | Hussey | ................ | G06K 7/10881 235/375 |
| 2009/0034731 A1 * | 2/2009 | Oshima | ................ | H04L 63/18 380/270 |

(56) References Cited

U.S. PATENT DOCUMENTS

| | | | |
|---|---|---|---|
| 2009/0082834 A1* | 3/2009 | Kalpin | H04L 63/0428 713/171 |
| 2009/0157141 A1* | 6/2009 | Chiao | A61N 1/37229 607/46 |
| 2009/0182388 A1* | 7/2009 | Von Arx | A61N 1/378 607/60 |
| 2009/0182426 A1* | 7/2009 | Von Arx | A61N 1/378 600/301 |
| 2009/0204019 A1* | 8/2009 | Ginggen | A61M 27/006 600/561 |
| 2010/0049009 A1 | 2/2010 | Muirhead | |
| 2010/0085160 A1* | 4/2010 | Fu | A61N 1/37223 607/60 |
| 2010/0211787 A1* | 8/2010 | Bukshpun | H04L 9/14 380/255 |
| 2010/0213082 A1* | 8/2010 | Feldman | C12Q 1/006 204/403.14 |
| 2010/0246602 A1* | 9/2010 | Barreto | H04L 69/18 370/476 |
| 2010/0250767 A1* | 9/2010 | Barreto | H04L 69/16 709/233 |
| 2010/0274218 A1 | 10/2010 | Yodfat et al. | |
| 2010/0315225 A1 | 12/2010 | Teague | |
| 2010/0328320 A1 | 12/2010 | Kerstna et al. | |
| 2011/0058485 A1* | 3/2011 | Sloan | G16H 40/67 370/242 |
| 2011/0178462 A1* | 7/2011 | Moberg | H04L 63/061 604/151 |
| 2011/0213225 A1 | 9/2011 | Bernstein et al. | |
| 2012/0046528 A1* | 2/2012 | Eigler | A61B 5/021 600/301 |
| 2012/0093315 A1* | 4/2012 | Nierzwick | H04L 63/061 380/270 |
| 2012/0109248 A1* | 5/2012 | Danielsson | A61N 1/3708 702/63 |
| 2012/0123227 A1* | 5/2012 | Sun | A61B 5/14532 600/309 |
| 2012/0182894 A1 | 7/2012 | Gaines et al. | |
| 2012/0182927 A1 | 7/2012 | Wiesner et al. | |
| 2012/0185268 A1 | 7/2012 | Wiesner et al. | |
| 2012/0242501 A1* | 9/2012 | Tran | A61B 5/0024 340/870.02 |
| 2013/0002448 A1* | 1/2013 | Makdissi | A61N 1/362 340/870.4 |
| 2013/0005246 A1* | 1/2013 | Waters | H04W 76/14 455/41.1 |
| 2013/0017791 A1* | 1/2013 | Wang | H04W 4/80 455/41.2 |
| 2013/0076531 A1* | 3/2013 | San Vicente | H04W 12/06 340/870.02 |
| 2013/0088365 A1* | 4/2013 | Scordilis | H04B 17/14 340/870.02 |
| 2013/0091238 A1* | 4/2013 | Liu | H04W 76/10 709/217 |
| 2013/0204100 A1* | 8/2013 | Acquista | A61B 5/14539 600/509 |
| 2013/0246783 A1* | 9/2013 | Ho | H04L 63/06 713/150 |
| 2013/0289334 A1* | 10/2013 | Badstibner | H01F 38/14 307/104 |
| 2013/0303942 A1* | 11/2013 | Damaser | A61B 5/03 600/561 |
| 2013/0318580 A1* | 11/2013 | Gudlavenkatasiva | H04L 63/08 726/7 |
| 2014/0039285 A1* | 2/2014 | Goodnow | A61B 5/1473 600/347 |
| 2014/0118769 A1* | 5/2014 | Adachi | H04N 1/00342 358/1.13 |
| 2014/0122878 A1* | 5/2014 | Cho | H04L 67/02 713/168 |
| 2014/0153017 A1* | 6/2014 | Watanabe | G06F 3/1212 358/1.13 |
| 2014/0204833 A1* | 7/2014 | Negishi | H04W 88/08 370/315 |
| 2014/0206976 A1* | 7/2014 | Thompson | G16Z 99/00 600/391 |
| 2014/0220960 A1* | 8/2014 | Nagel | H04W 24/10 455/466 |
| 2014/0266933 A1* | 9/2014 | Andersen | H01Q 7/00 343/718 |
| 2014/0270801 A1* | 9/2014 | Sleator | H04B 10/25752 398/140 |
| 2014/0273824 A1* | 9/2014 | Fenner | H04B 5/79 455/41.1 |
| 2014/0275843 A1* | 9/2014 | Piccirillo | A61B 5/14556 600/316 |
| 2014/0275859 A1* | 9/2014 | Tankiewicz | A61B 5/076 600/302 |
| 2014/0358535 A1* | 12/2014 | Lee | G10L 17/22 704/233 |
| 2014/0365781 A1* | 12/2014 | Dmitrienko | G06F 21/335 713/185 |
| 2015/0018643 A1* | 1/2015 | Cole | A61B 5/0015 600/316 |
| 2015/0026796 A1* | 1/2015 | Alan | G06F 21/31 726/19 |
| 2015/0036823 A1* | 2/2015 | Graube | H04W 12/04 380/46 |
| 2015/0049871 A1 | 2/2015 | Xie et al. | |
| 2015/0117645 A1* | 4/2015 | Carlson | H04L 9/0838 380/262 |
| 2015/0121063 A1* | 4/2015 | Maller | H04L 63/0435 713/153 |
| 2015/0126109 A1* | 5/2015 | Keshavdas | H04B 5/72 455/41.1 |
| 2015/0127549 A1* | 5/2015 | Khan | G06Q 20/3278 705/71 |
| 2015/0127550 A1* | 5/2015 | Khan | G06Q 20/3278 705/44 |
| 2015/0143118 A1* | 5/2015 | Sheller | H04L 9/14 713/168 |
| 2015/0199288 A1* | 7/2015 | DeHennis | G06F 1/3209 506/39 |
| 2015/0256338 A1* | 9/2015 | Roberts | H04W 12/50 713/171 |
| 2015/0261972 A1* | 9/2015 | Lee | H04L 9/088 713/165 |
| 2015/0264732 A1* | 9/2015 | Satoh | H04W 76/14 455/41.1 |
| 2015/0290379 A1* | 10/2015 | Rudser | A61N 1/3787 600/16 |
| 2015/0297081 A1* | 10/2015 | Fuchs | H04W 40/02 340/870.07 |
| 2015/0304851 A1* | 10/2015 | Chen | H04L 63/0853 713/172 |
| 2015/0319563 A1* | 11/2015 | Johnson | H04W 40/244 455/456.3 |
| 2015/0355245 A1* | 12/2015 | Ordanis | G01R 31/42 702/62 |
| 2016/0028874 A1 | 1/2016 | Mankopf et al. | |
| 2016/0034707 A1* | 2/2016 | Sahu | H04L 9/0866 713/168 |
| 2016/0066808 A1* | 3/2016 | Hijazi | A61B 5/333 600/382 |
| 2016/0072781 A1* | 3/2016 | Zhang | H04L 67/1044 726/4 |
| 2016/0144193 A1* | 5/2016 | Doerr | A61N 1/3987 607/32 |
| 2016/0149919 A1* | 5/2016 | Gauthier | H04L 43/16 726/7 |
| 2016/0156599 A1 | 6/2016 | Son et al. | |
| 2016/0166564 A1* | 6/2016 | Myers | A61K 9/007 392/386 |
| 2016/0171486 A1* | 6/2016 | Wagner | G06Q 20/326 705/39 |
| 2016/0183836 A1* | 6/2016 | Muuranto | G16H 40/67 600/300 |
| 2016/0219805 A1* | 8/2016 | Romney | A01G 25/16 |

(56) References Cited

U.S. PATENT DOCUMENTS

| | | | |
|---|---|---|---|
| 2016/0225374 A1* | 8/2016 | Rodriguez | G10L 17/10 |
| 2016/0315762 A1* | 10/2016 | Moon | H04L 9/065 |
| 2016/0331232 A1* | 11/2016 | Love | A61B 5/14532 |
| 2016/0331952 A1* | 11/2016 | Faltys | G16H 40/63 |
| 2016/0366181 A1* | 12/2016 | Smith | G06F 21/6236 |
| 2016/0374124 A1* | 12/2016 | Gothe | A61N 1/37217 |
| 2017/0005820 A1* | 1/2017 | Zimmerman | H04L 67/10 |
| 2017/0019765 A1* | 1/2017 | Hoyer | H04W 12/082 |
| 2017/0083117 A1* | 3/2017 | Ha | G06F 3/0383 |
| 2017/0086248 A1* | 3/2017 | Sloan | H04B 7/26 |
| 2017/0136834 A1* | 5/2017 | Chong | B60C 23/0433 |
| 2017/0148018 A1* | 5/2017 | Levin | G06Q 20/202 |
| 2017/0281060 A1* | 10/2017 | Wedekind | A61B 5/4839 |
| 2017/0340254 A1* | 11/2017 | Davis | H04B 5/77 |
| 2018/0028827 A1* | 2/2018 | Schilling | A61N 1/37223 |
| 2018/0035374 A1* | 2/2018 | Borden | H04W 28/0278 |
| 2018/0039775 A1* | 2/2018 | Poiesz | G06F 9/468 |
| 2018/0052884 A1* | 2/2018 | Kale | G06F 16/242 |
| 2018/0137070 A1* | 5/2018 | DeHennis | H02J 50/10 |
| 2018/0176007 A1* | 6/2018 | Kountouris | H04L 9/0819 |
| 2018/0219869 A1* | 8/2018 | Kumar | H04W 4/025 |
| 2018/0234133 A1* | 8/2018 | Biederman | H04B 5/79 |
| 2018/0338726 A1 | 11/2018 | Yarger et al. | |
| 2019/0142315 A1* | 5/2019 | Love | A61B 5/14532 600/316 |
| 2020/0053121 A1* | 2/2020 | Wilcox | G06F 40/289 |
| 2020/0065459 A1* | 2/2020 | Himabindu | G06F 21/316 |
| 2020/0074338 A1* | 3/2020 | Florentino | G06N 7/01 |
| 2020/0138288 A1* | 5/2020 | Al-Ali | A61B 5/0024 |
| 2020/0167785 A1* | 5/2020 | Kursun | H04L 43/045 |
| 2021/0065245 A1* | 3/2021 | Resheff | G06F 16/9035 |
| 2022/0131844 A1* | 4/2022 | Sherlock | H04L 63/105 |
| 2022/0284082 A1* | 9/2022 | Liu | G06F 21/31 |
| 2022/0351142 A1* | 11/2022 | McGarr | H04L 51/216 |
| 2022/0400130 A1* | 12/2022 | Kapoor | H04L 63/10 |
| 2023/0004972 A1* | 1/2023 | Rapowitz | G06Q 20/4014 |
| 2023/0012250 A1* | 1/2023 | Miller | H04L 63/10 |
| 2023/0053675 A1* | 2/2023 | Edwards | G06F 21/31 |
| 2023/0098536 A1* | 3/2023 | Zheng | G06F 21/6209 726/19 |
| 2023/0333528 A1* | 10/2023 | Biswas | G05B 19/042 |
| 2023/0342374 A1* | 10/2023 | Sitsky | G06F 9/44521 |

OTHER PUBLICATIONS

U.S. Appl. No. 15/367,311, Final Office Action, Mailed on Jan. 27, 2020, 20 pages.

U.S. Appl. No. 15/367,311, Non-Final Office Action, Mailed on Oct. 17, 2018, 10 pages.

U.S. Appl. No. 15/367,311, Non-Final Office Action, Mailed on Aug. 8, 2019, 17 pages.

U.S. Appl. No. 15/367,311, Notice of Allowance, Mailed on May 25, 2022, 20 pages.

Aboelfotoh et al., "A Mobile-based Architecture for Integrating Personal Health Record Data", 2014 IEEE 16th International Conference on e-Health Networking, Applications and Services (Healthcom), 2014, pp. 269-274.

Coates et al., "Medical Remote Sensors in Tactical Networks", Naval Postgraduate School, Available online at http://hdl.handle.net/10945/45170, Mar. 2015, 72 pages.

Dehennis et al., "An Integrated Wireless Fluorimeter for a Long Term Implantable, Continuous Glucose Monitoring System", Diabetes Technology & Amp Therapeutics, 2013, 1 page.

Jara et al., "Evaluation of Bluetooth Low Energy Capabilities for Tele-mobile Monitoring in Home-care", Journal of Universal Computer Science, vol. 9, No. 9, 2013, pp. 1219-1241.

Leone et al., "An Open NFC-based Platform for Vital Signs Monitoring", 2015 XVIII AISEM Annual Conference, 2015, 4 pages.

Lopez et al., "Survey of Internet of Things Technologies for Clinical Environments", IEEE, 27th International Conference on Advanced Information Networking and Applications Workshops, 2013, pp. 1349-1354.

Morak et al., "Design and Evaluation of a Telemonitoring Concept Based on NFC-Enabled Mobile Phones and Sensor Devices", IEEE Transactions on Information Technology in Biomedicine, vol. 16, No. 1, Jan. 2012, pp. 17-23.

Nesheim, "The Ble Cloaker: Securing Implantable Medical Device Communication Over Bluetooth Low Energy Links", The Faculty of California Polytechnic State University, Available Online at: https://digitalcommons.calpoly.edu/theses/1486, Sep. 2015, 63 pages.

Patil et al., "Telemonitoring Physiological Parameters of a Patient from a Distance by Near Field Communication Mobile", IEEE, Fourth International Conference on Advanced Computing & Communication Technologies, 2014, pp. 345-349.

Strommer et al., "Application of Near Field Communication for Health Monitoring in Daily Life", International Conference of the IEEE Engineering in Medicine and Biology Society, 2006, pp. 3246-3249.

Suzuki et al., "Wearable Wireless Vital Monitoring Technology for Smart Health Care", IEEE 2013 7th International Symposium on Medical Information and Communication Technology (ISMICT), 2013, 4 pages.

Villarreal et al., "A Proposal for Mobile Diabetes Self-control: Towards a Patient Monitoring Framework", Springer, International Work-Conference on Artificial Neural Networks, 2009, pp. 870-877.

Zemerly et al., "Security and Privacy Framework for Ubiquitous Healthcare IoT Devices", IEEE, 10th International Conference for Internet Technology and Secured Transactions (ICITST), 2015, pp. 70-75.

Zhang et al., "Towards Trustworthy Medical Devices And Body Area Networks", 50th ACM/EDAC/IEEE Design Automation Conference (DAC), 2013, pp. 1-6.

Zhang et al., "Trustworthiness of Medical Devices and Body Area Networks", Proceedings of the IEEE, vol. 102, No. 8, Aug. 2014, pp. 1174-1188.

\* cited by examiner

NFC BEACONS FOR BIDIRECTIONAL COMMUNICATION BETWEEN AN ELECTROCHEMICAL SENSOR AND A READER DEVICE

CROSS-REFERENCE TO RELATED APPLICATION

This application is a Continuation of U.S. application Ser. No. 15/367,311, filed on Dec. 2, 2016 which makes reference to and claims priority to U.S. Provisional Application No. 62/264,403, filed on Dec. 8, 2015, both of which are incorporated herein by reference in their entirety.

BACKGROUND

Unless otherwise indicated herein, the materials described in this section are not prior art to the claims in this application and are not admitted to be prior art by inclusion in this section.

Many various radio technologies exist to enable wireless communication between devices. The various radio technologies operate with different frequencies of operation, different power requirements, different signaling, different data rates, and other different radio parameters. During the design process of a wireless device, a radio technology may be selected based on the specific requirement of the wireless device.

Some wireless devices are of sufficiently small size that a large power supply cannot reasonably accompany the device. In these instances, the electronic device may receive power from an external power source. For example, in a typical Radio-frequency identification (RFID) implementation, an RFID chip receives power externally via an antenna to power the chip. Further, the same antenna may be used to both supply power and communication data to the RFID chip. Therefore, the external power source may be configured to supply power to the electronic device wirelessly.

Additionally, some electronic devices may be mounted or placed in locations with space constraints. Therefore, it may be desirable for a device to have a form factor compatible with associated space constraints. For example, the size of the wireless device may in part dictate a frequency range of operation of a device.

SUMMARY

Disclosed herein are examples that relate to a sensing device. The sensing device includes a sensor, a memory, a processor, and two radio units. A first radio unit of the two radio units is configured for bidirectional communication with an external device using a first radio communication protocol. The bidirectional communication comprises receiving configuration data from the external device via a first radio signal from the external device. The second radio unit of the two radio units is configured for unidirectional communication with the external device using a second radio communication protocol. The unidirectional communication comprises the second radio unit transmitting a second radio signal to the external device. The second radio signal communicates data including one or more measurements obtained by the sensor.

In another aspect, the present application describes a method. The method includes powering a sensing device using radio frequency energy from an external device. The sensing device includes a sensor, a memory, a processor, a first radio unit configured for bidirectional communication with the external device using a first radio communication protocol and a second radio unit configured for unidirectional communication with the external device using a second radio communication protocol. The method further includes receiving, by the first radio unit, configuration data from the external device. Additionally, the method includes storing the configuration data in the memory. Furthermore, the method includes obtaining one or more measurements using the sensor. And, the method also includes transmitting, by the second radio unit, data to the external device, wherein the data comprises the one or more measurements.

In yet another example, another method for a sensing device is provided, where the sensing device includes a sensor, a memory, a first radio unit, and a second radio unit. The method may include obtaining a plurality of measurements using the sensor. The method also includes storing data in the memory, where the data stored in the memory comprises the plurality of measurements obtained by the sensor. Further, the method includes transmitting, by a second radio unit, a plurality of advertisement packets to an external device, wherein the second radio unit does not have data reception capabilities. Additionally, the method includes receiving, by the first radio unit, a data request from the external device. And, the method also includes transmitting, by the first radio unit, the data stored in the memory to the external device in response to the data request.

The foregoing summary is illustrative only and is not intended to be in any way limiting. In addition to the illustrative aspects, examples, and features described above, further aspects, examples, and features will become apparent by reference to the figures and the following detailed description.

DETAILED DESCRIPTION

Figure 1:
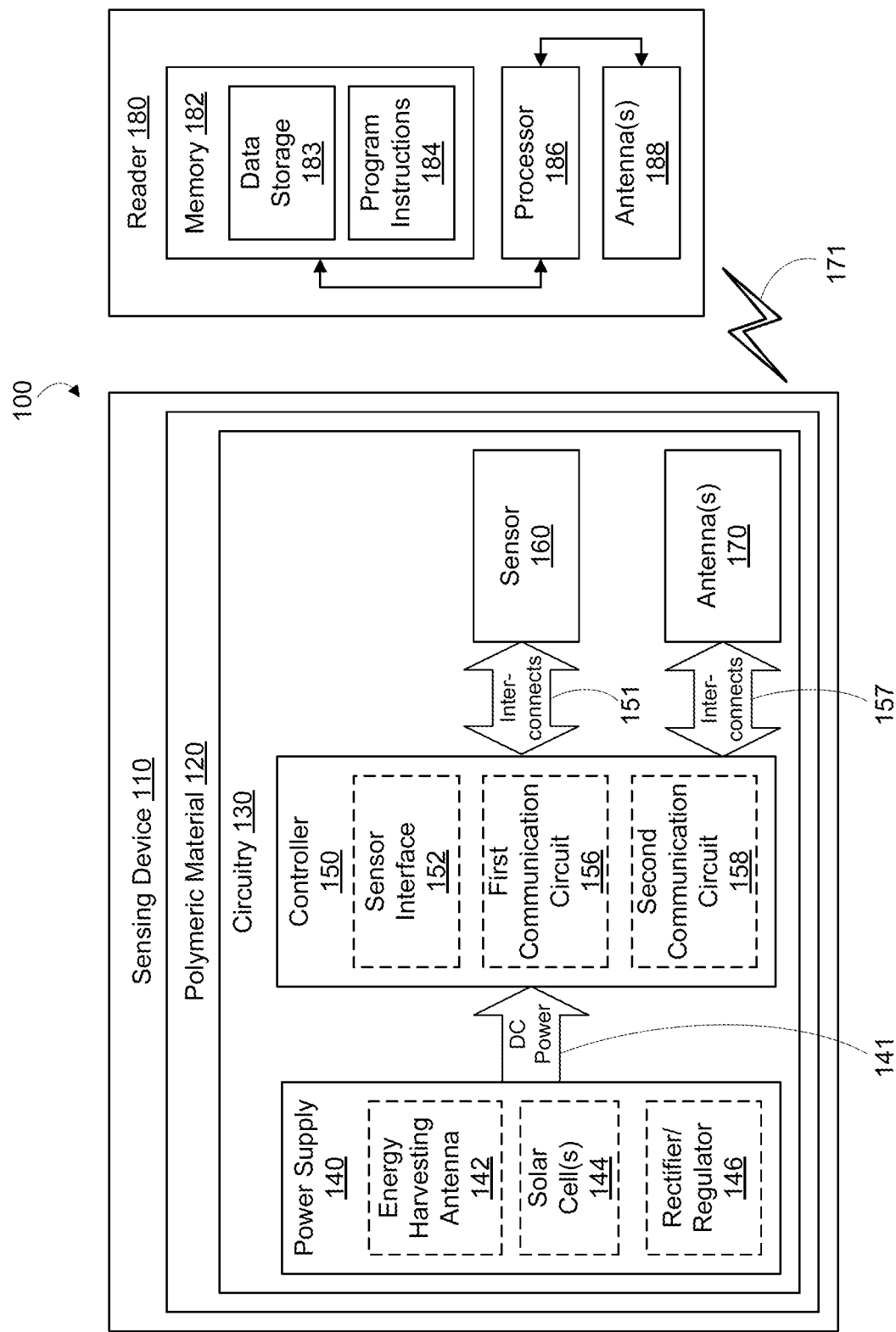
FIG. 1 is a block diagram of an example system that includes a sensing device in wireless communication with a reader, in accordance with an example embodiment.

In the following detailed description, reference is made to the accompanying figures, which form a part hereof. In the figures, similar symbols typically identify similar components, unless context dictates otherwise. The illustrative examples described in the detailed description, figures, and claims are not meant to be limiting. Other examples may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

One aspect of the present disclosure provides a medical sensing device that includes two different radio technologies for communication with an external device. The medical sensing device of the present disclosure may be implantable, wearable, body-mountable, or any other configuration that enables the medical sensing device to make measurements. By using two different radio technologies, advantages of each respective technology may be used to increase device performance. The sensing device may include a memory, a processor, and two radio units (a first radio unit and a second radio unit). The first radio unit may operate with a first radio technology, such as a Near Field Communication (NFC) based radio technology. The first radio unit may be configured to receive a radio signal from an external computing device and to communicate with the external computing device (external reader). In some examples, the first radio unit may also be configured to power a component configured to supply power to the memory, the processor, the first radio unit, and the second radio unit. The second radio unit may operate with a second radio technology, such as a Bluetooth Low Energy based radio technology. During the operation of the device, the second radio unit is configured to communicate information from the memory to the external computing device. Additionally, in some examples, the second radio unit does not have receiving capabilities. The second radio unit may be just a radio transmitter. By not having a radio receiver, the power requirements of the second radio unit may be reduced. Further, the second radio unit may communicate data by way of an advertisement packet.

During the operation of the device, the first radio unit may be used for data exchange between an external reader and the device and the second radio unit may be used to transmit information from the device to the external reader. The sensing device may include a sensor configured to make measurements, such as measurements of glucose levels in a bodily fluid. The second radio unit may be configured to periodically transmit one or more of the measurements (e.g., glucose levels) obtained by the sensor. The first radio unit may be configured to communicate with an external reader to provide a dataset of historical measurements obtained by the sensor. For example, the dataset may be in a bulk data transmission and include a large amount of data samples, such as a day's worth of periodically-sampled glucose levels. Although the present disclosure uses glucose as one example, other types of sensors may be used to make other measurements well.

In some examples, the information received from the external computing device comprises an encryption key. The processor of the device may store the encryption key in the memory. During operation of the device, the information communicated by the second radio unit may be encoded with the encryption key. In some other examples, the information received from the external computing device includes a pairing key. The processor of the device may store the pairing key in the memory. During operation of the device, the second radio communicates with the external computing device based on the pairing key.

An external reader device or "reader" can radiate radio frequency radiation to power the sensing device. The sensing device may include a sensor, and the reader may control the operation of the sensor by controlling the supply of power to the sensing device. In some examples, the reader can operate to intermittently interrogate the sensing device to provide a reading by radiating sufficient radiation to power the sensing device to obtain a measurement and communicate the result.

The sensing device can be configured with, or be part of, a NFC radio-based system, such as a Radio-frequency Identification (RFID) tag. The RFID tag and reader can communicate using an RFID protocol; e.g., an RFID Generation 2 protocol. The RFID tag can be configured to receive radio signals from the reader. In some embodiments, the reader's signals can be used for both communicating with and powering the RFID tag; while in other embodiments, the RFID tag can be a powered device; e.g., be configured with a battery that powers the tag. In embodiments, where a battery powers the tag, the reader's signals may be used to charge the battery. Therefore, the battery may be wirelessly charged in situ.

The reader can communicate with other devices than the RFID tag. As one possible example, the reader can be equipped with a Bluetooth interface, such as Bluetooth Low Energy, as well as with an RFID interface. The reader can communicate with other devices, e.g., a display device, via a Bluetooth or other protocol. In one example, the reader can obtain data from the RFID tag using RFID command(s); e.g., the RFID Generation 2 standard Read command. Upon obtaining the data, the reader can store, process, and/or communicate the data using the Bluetooth interface to another device, such as the display device. Other interfaces for communicating with devices using other communication protocol(s) are possible as well.

As an example, the above-mentioned sensing device can be configured with a sensor. The sensor can be configured to take measurements while implanted (e.g., implanted in tissue beneath a skin surface). Upon taking the measurements, the sensor may store data related to the measurements, and subsequently send the data upon request from the reader. The sensor could be an optical sensor, an electrochemical sensor, a temperature sensor, a pressure sensor, or some other type of sensor. A previously discussed, the medical sensing device of the present disclosure may be implantable, wearable, body-mountable, or any other configuration that enables the medical sensing device to make measurements.

The present disclosure may be advantageous over traditional devices because the present disclosure enables a sensing device with reduced complexity, improved security, and reduced processing requirements compared to traditional devices. In example embodiments, complexity of the sensing device is reduced by providing one of the two radio units with only a transmitter. By lowing the complexity of the sensing device, the power used by the sensing device may be reduced as well. Security may be improved in example embodiments because one of the radio technologies operates in a transmission-only mode. In some examples, long range communications may be performed in a transmission-only mode (such as by way of Bluetooth Low Energy advertisement packs), so devices that are not located near the sensing device cannot communicate data to the sensing device. Therefore, in order to communicate data to the sensing device, or to receive data other than that communicated by the transmit-only radio, one would need to be physically close to the sensing device. Yet further, the processing requirements for the sensing device may be reduced. When the device is operating in the transmission-only mode, it will only transmit a data signal. It will not be receiving any signals, so it will not be performing any type of acknowledgement receipt. For example, a sensing device may be configured to transmit a sensor reading value once every 60 seconds. The sensing device may transmit the sensor reading and not wait for any confirmation that the signal was received. Therefore, in transmission-only mode, the sensing device may act a beacon that transmits sensor data periodically.

FIG. 1 is a block diagram of a system 100 that includes a sensing device 110 in wireless communication with a reader 180. The sensing device 110 could be, for example, a body-worn device. In some examples, the body-worn device may be implanted in tissue beneath the skin surface. The reader 180 may be able to wirelessly communicate with and/or wirelessly power the sensing device 110 when it is body-worn in this way. Alternatively, the sensing device 110 could be configured to be mounted on an external skin surface (e.g., as a patch) or could be configured as some other type of body-mountable device. Other configurations and applications of sensing device 110 are possible as well.

The sensing device 110 may include circuitry 130 (e.g., in the form of a microchip) that is embedded in a polymeric material 120. The sensing device 110 may have dimensions that facilitate being embedded in tissue beneath a skin surface. For example, the sensing device 110 can be shaped as a square or rectangle with a length on each side on the order of 100s of micrometers and a thickness of about 50 micrometers. Alternatively, sensing device 110 may be configured for mounting to an external skin surface. For example, polymeric material 120 may include an adhesive or other means for attaching the sensing device 110 to skin.

The circuitry 130 may include a power supply 140, a controller 150, a sensor 160, and communication antenna(s) 170. The power supply 140 supplies operating voltages (e.g., DC power 141) to the controller 150 and/or the sensor 160. The antenna(s) 170 is operated by the controller 150 to communicate information to and/or from the sensing device 110.

The power supply 140 is configured to harvest ambient energy to power the controller 150 and sensor 160. For example, a radio-frequency energy-harvesting antenna 142 can capture energy from incident radio radiation. Additionally or alternatively, solar cell(s) 144 ("photovoltaic cells") can capture energy from incoming ultraviolet, visible, and/or infrared radiation. Furthermore, an inertial power scavenging system can be included to capture energy from ambient vibrations. The energy harvesting antenna 142 can optionally be a dual-purpose antenna that is also used to communicate information to the reader 180. That is, the functions of the communication antenna(s) 170 and the energy harvesting antenna 142 can be accomplished with the same physical antenna. In some examples, there may be multiple communication and and/or the energy harvesting antenna(s) 142. In one example, communication antenna(s) 170 may operate with a first radio communication technology and the energy harvesting antenna 142 may operate with a second radio communication technology.

A rectifier/regulator 146 can be used to condition the captured energy to a stable DC supply voltage 141 that is supplied to the controller 150. For example, the energy harvesting antenna 142 can receive incident radio frequency radiation. Varying electrical signals on the leads of the antenna 142 are output to the rectifier/regulator 146. The rectifier/regulator 146 rectifies the varying electrical signals to a DC voltage and regulates the rectified DC voltage to a level suitable for operating the controller 150. Additionally or alternatively, output voltage from the solar cell(s) 144 can be regulated to a level suitable for operating the controller 150. The rectifier/regulator 146 can include one or more energy storage devices to mitigate high frequency variations in the ambient energy gathering antenna 142 and/or solar cell(s) 144. For example, one or more energy storage devices (e.g., a capacitor, an inductor, etc.) can be connected in parallel across the outputs of the rectifier 146 to regulate the DC supply voltage 141 and configured to function as a low-pass filter.

The controller 150 is turned on when the DC supply voltage 141 is provided to the controller 150, and the logic in the controller 150 operates the sensor 160 and the antenna(s) 170. The controller 150 can include logic circuitry configured to operate the sensor 160 so as to interact with the antenna(s) 170. The impedance of the antenna(s) 170 may be used to communicate via backscatter radiation. Antenna(s) 170 and backscatter radiation are discussed further below.

In one example, the controller 150 includes a sensor interface module 152 that is configured to interface with the sensor 160. The sensor 160 can be, for example, a sensor configured to measure one or more physiological properties, such as pulse rate, blood oxygenation, blood pressure, or the concentration of glucose or other analyte. The sensor 160 could be, for example, an optical sensor or an electrochemical sensor.

The controller 150 can also include a communication circuit 156 for sending and/or receiving information via the antenna(s) 170. The communication circuit 156 can optionally include one or more oscillators, mixers, frequency injectors, etc. to modulate and/or demodulate information on a carrier frequency to be transmitted and/or received by the antenna(s) 170. As previously stated, in some examples, the sensing device 110 is configured to indicate a measurement obtained by sensor 160 by modulating an impedance of the antenna(s) 170 in a manner that is perceivable by the reader 180. For example, the communication circuit 156 can cause variations in the amplitude, phase, and/or frequency of backscatter radiation from the antenna 170, and such variations can be detected by the reader 180.

It is noted that the block diagram shown in FIG. 1 is described in connection with functional modules for convenience in description. However, embodiments of the sensing device 110 can be arranged with one or more of the functional modules ("sub-systems") implemented in a single chip, integrated circuit, and/or physical component. For example, while the rectifier/regulator 146 is illustrated in the power supply block 140, the rectifier/regulator 146 can be implemented in a chip that also includes the logic elements of the controller 150 and/or other features of the embedded electronics in the sensing device 110. Thus, the DC supply voltage 141 that is provided to the controller 150 from the power supply 140 can be a supply voltage that is provided to components on a chip by rectifier and/or regulator components located on the same chip. That is, the functional blocks in FIG. 1 shown as the power supply block 140 and controller block 150 need not be implemented as physically separated modules. Moreover, one or more of the functional modules described in FIG. 1 can be implemented by separately packaged chips electrically connected to one another.

Additionally or alternatively, the energy harvesting antenna 142 and the communication antenna(s) 170 can be implemented with the same physical antenna. For example, a loop antenna can both harvest incident radiation for power generation and communicate information via backscatter radiation. As previously stated, in one example, communication antenna(s) 170 may operate with a first radio communication technology and the energy harvesting antenna 142 may operate with a second radio communication technology. In yet another example, communication antenna(s) 170 may include one antenna configured to operate with a first radio communication technology and a second antenna configured to operate with a second radio communication technology.

The reader 180 can be configured to be external to the wearer; i.e., is not part of the sensing device. Reader 180 can include one or more antennas 188 to send and receive wireless signals 171 to and from the sensing device 110. In some embodiments, reader 180 can communicate using hardware and/or software operating according to one or more standards, such as, but not limited to, an NFC standard, an RFID standard, a Bluetooth standard, a Wi-Fi standard, a Zigbee standard, etc. Further, the reader 180 can communicate using hardware and/or software operating according to a modified version of one or more standards. When a standard is discussed within the present disclosure, it is meant to include any modifications to communications based on the standard that may not explicitly be included in the standard.

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the sensor 160), program settings (e.g., to adjust behavior of the sensing device 110 and/or reader 180), etc. The memory 182 can also include program instructions 184 for execution by the processor 186 to cause the reader 180 to perform processes specified by the instructions 184. For example, the program instructions 184 can cause reader 180 to provide a user interface that can convey information communicated from the sensing device 110 (e.g., information relating to measurements obtained by the sensor 160). The reader 180 can also include one or more hardware components for operating the antenna 188 to send and receive the wireless signals 171 to and from the sensing device 110. For example, oscillators, frequency injectors, encoders, decoders, amplifiers, filters, etc. can drive the antenna 188 according to instructions from the processor 186.

In some embodiments, reader 180 can be a smart phone, digital assistant, or other portable computing device with wireless connectivity sufficient to provide the wireless communication link 171. In other embodiments, reader 180 can be implemented as an antenna module that can be plugged into a portable computing device; e.g., in scenarios where the communication link 171 operates at carrier frequencies not commonly employed in portable computing devices. In even other embodiments, the reader 180 can communicate with an external display device via a wired or wireless connection.

Figure 2A:
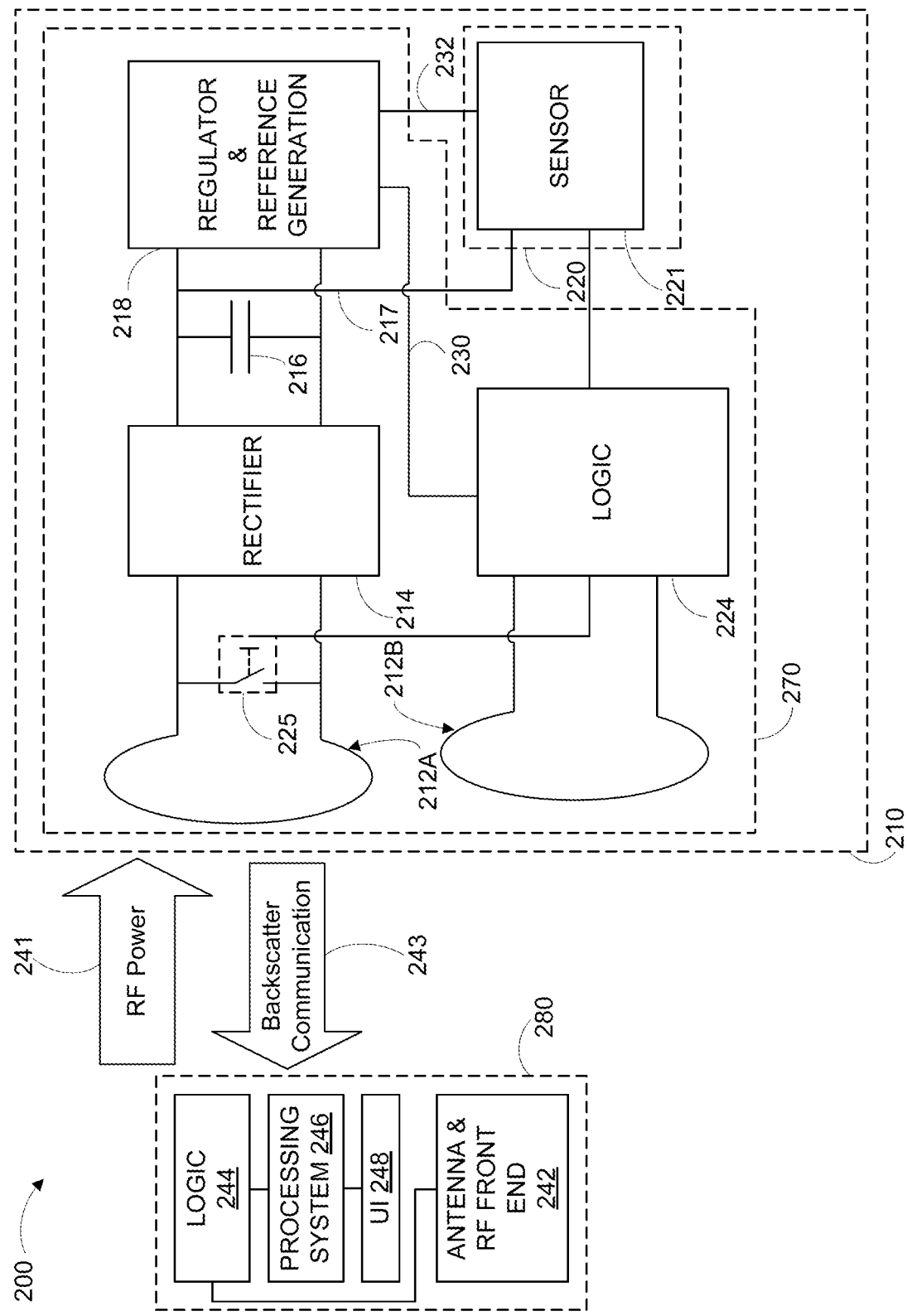
FIG. 2A is a functional block diagram of an example system that includes a sensing device, in accordance with an example embodiment.

FIG. 2A is a functional block diagram of a system 200 that includes a sensing device 210 with embedded electronic components in communication with and powered by reader 280. Reader 280 can also be configured to communicate with a display device (the display device may or may not be integrated with the reader 280 as UI 248). Reader 280 and sensing device 210 can communicate according to one communication protocol or standard, shown in FIG. 2 as RF Power 241. In one particular embodiment, the protocol used for RF Power 241 and Backscatter communication 243 is an RFID protocol. The sensing device 210 includes an antenna 212A for capturing radio frequency (RF) power 241 from the reader 280. The antenna 212A may also create backscatter communication 243.

The sensing device 210 includes rectifier 214, energy storage 216 (that may output unregulated voltage 217), and regulator 218 for generating regulated supply voltages 230, 232 to operate the embedded electronics. The sensing device 210 includes a sensor 221 that may have a sensor interface 220. The sensing device 210 includes hardware logic 224 for communicating results from the sensor 221 to the reader 280 by modulating the impedance of the antenna 212A. An impedance modulator 225 (shown symbolically as a switch in FIG. 2) can be used to modulate the antenna impedance according to instructions from the hardware logic 224. Similar to the sensing device 110 discussed above in connection with FIG. 1, in some examples, the sensing device 210 can be embedded within a polymeric material configured to be body-worn in tissue beneath a skin surface or externally mounted on a skin surface.

With reference to FIG. 2, in various embodiments, the sensor 221 may be configured to make various measurements, including but not limited to physiological measurements of a person in which the device is body-worn, or making other measurements of the person in which the device is body-worn. The connections shown in FIG. 2 are one example of possible configurations for the sensor 221. The sensor interface 220 may be configured as a part of the sensor 221 itself. For example, the sensor interface 220 may convert the output of the sensor 221 into a format that in understandable by the hardware logic 224.

The rectifier 214, energy storage 216, and voltage regulator 218 operate to harvest energy from received RF power 241. RF power 241 causes radio frequency electrical signals on leads of the antenna 212. The rectifier 214 is connected to the antenna leads and converts the radio frequency electrical signals to a DC voltage. The energy storage 216 (e.g., capacitor) is connected across the output of the rectifier 214 to filter out high frequency components of the DC voltage. The regulator 218 receives the filtered DC voltage (e.g. unregulated voltage 217) and outputs both a regulated supply voltage 230 to operate the hardware logic 224 and a regulated supply voltage 232 to operate the sensor 221 of the sensor interface 220. For example, the supply voltage can be equivalent to the voltage of the energy storage 216. In another example, the supply voltage can be equivalent to the voltage of the rectified DC voltage from the rectifier 214. Additionally, the regulated supply voltage 230 can be a voltage suitable for driving digital logic circuitry, such as approximately 1.2 volts, approximately 3 volts, etc. The voltage needed as the regulated supply voltage 230 may change depending on a functionality requirement of the logic 224 (or a voltage requirement of other components of the sensing device 210). Reception of the RF power 241 from the reader 280 (or another source, such as ambient radiation, etc.) causes the regulated supply voltages 230, 232 to be supplied to the sensor 220 and hardware logic 224. While powered, the sensor 220 and hardware logic 224 are configured to generate and measure a voltage (such as either unregulated voltage 217 or regulated supply voltages 232) and communicate the results.

The sensor results can be communicated back to the reader 280 via backscatter radiation 243 from the antenna 212. The hardware logic 224 receives the supply voltage from the sensor interface 220 (or the sensor 221 itself) and modulates (225) the impedance of the antenna 212A. The antenna impedance and/or change in antenna impedance are detected by the reader 280 via the backscatter signal 243.

The sensor results can be communicated back to the reader 280 via radiation 243 from the antenna 212B. The hardware logic 224 receives the supply voltage from the sensor interface 220 (or the sensor 221 itself) and encodes the data for transmission by antenna 212B. The antenna 212B may be used with a radio technology that does not communication via backscatter radiation but rather emits it on radio radiation.

Reader 280 can include an antenna and RF front end 242 and logic components 244 to communicate using a radio protocol, decode the information indicated by the backscatter signal 243, provide digital inputs to a processing system 246 and receive inputs and/or provide outputs via user interface 248. The radio protocol can be, for example, an RFID protocol. In some embodiments, part or all of sensing device 210 can be configured to perform some or all features of an RFID tag. The tag may also be operable to communicate via a second radio protocol, which can be, for example, a Bluetooth-based protocol. In some embodiments, part or all of sensing device 210 can be configured to perform some or all features of a Bluetooth-protocol based tag. As previously discussed, each radio protocol may operate with a different antenna of antenna 212A and 212B. For example, as shown in FIG. 2, some or all of the components shown as tag 270 of sensing device 210 can perform some or all features of an RFID tag; e.g., antenna 212A, rectifier 214, energy storage 216, voltage regulator 218, hardware logic 224, etc.

In some embodiments, one or more of the features shown as separate functional blocks can be implemented ("packaged") on a single chip. For example, the sensing device 210 can be implemented with the rectifier 214, energy storage 216, voltage regulator 218, sensor interface 220, and the hardware logic 224 packaged together in a single chip or controller module. Such a controller can have interconnects ("leads") connected to the loop antenna 212 and the sensor electrodes 222, 223. Such a controller operates to harvest energy received at the antenna 212A, measure the supply voltage created by the harvested energy, and indicate the measured supply voltage via the antenna 212A (e.g., through the backscatter communication 243).

A processing system, such as, but not limited to, processing system 246 or processing system 256, can include one or more processors and one or more storage components. Example processor(s) include, but are not limited to, CPUs, Graphics Processing Units (GPUs), digital signal processors (DSPs), application specific integrated circuits (ASICs). Example storage component(s) include, but are not limited to volatile and/or non-volatile storage components, e.g., optical, magnetic, organic or other memory, disc storage; Random Access Memory (RAM), Read-Only Memory (ROM), flash memory, optical memory unit, and disc memory. The storage component(s) can be configured to store software and data; e.g., computer-readable instructions configured, when executed by a processor of the processing system, to cause the processing system to carry out functions such as but not limited to the herein-described functions of reader 280 or sensing device 210.

The reader 280 can associate the backscatter signal 243 with the sensor result (e.g., via the processing system 246 according to a pre-programmed relationship associating impedance of the antenna 212A with output from the sensor 220). The processing system 246 can then store the indicated sensor results (e.g., glucose levels) in a local memory and/or an external memory. The processing system 246 can store sensor results in the memory in a variety of ways. In some examples, the memory may store the measurements from the sensor (i.e. raw sensor data). In other examples, the processing system 246 may store data related to the sensor measurements in the memory (i.e. processed sensor data). The processed sensor data may be a time-average or other statistical summary of individual measurements over a discrete interval of time of measurements from the sensor. The processing system 246 may also store data in the memory at various time intervals. For example, the processing system 246 may store data in the memory once a minute. The processing system 246 may store raw sensor data or processed sensor data in the memory at each interval. Thus, the memory may contain data stored in a time series.

User interface 248 of reader 280 can include an indicator, such as but not limited to one or more light-emitting diodes (LEDs) and/or speakers, that can indicate that reader 280 is operating and provide some information about its status. For example, reader 280 can be configured with an LED that displays one color (e.g., green) when operating normally and another color (e.g., red) when operating abnormally. In other embodiments, the LED(s) can change display when processing and/or communicating data in comparison to when idle (e.g., periodically turn on and off while processing data, constantly stay on or constantly stay off while idle). The reader 280 may also provide an audio output.

Figure 2B:
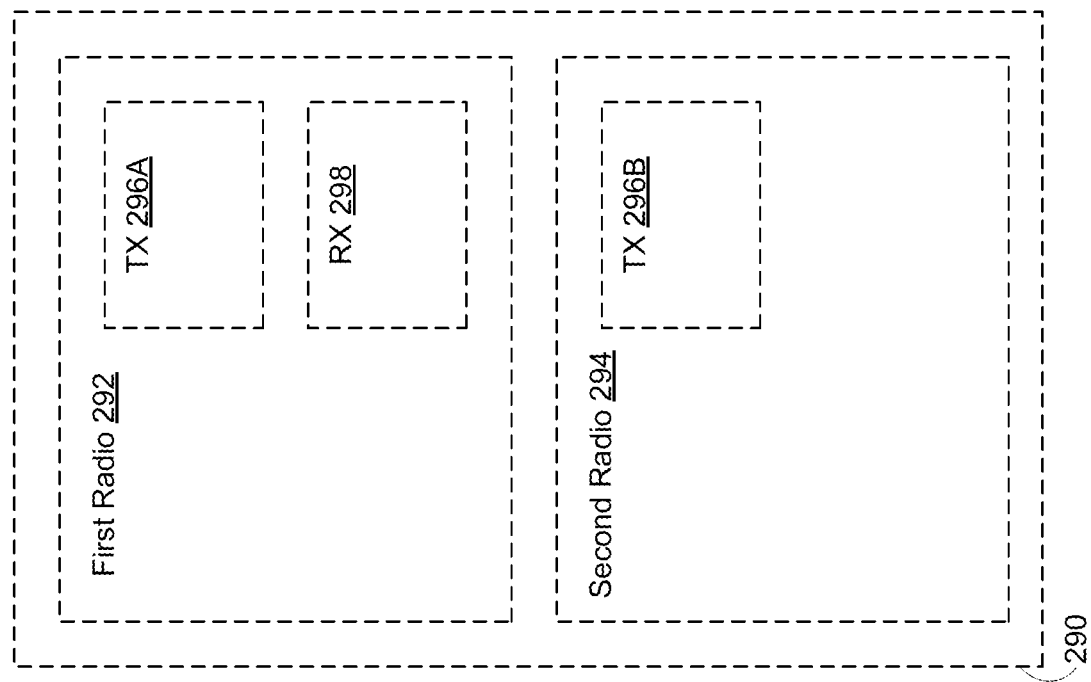
FIG. 2B is a functional block diagram of an example radio system of a sensing device that is powered by and in communication with an external reader, in accordance with an example embodiment.

FIG. 2B is a functional block diagram of an example radio system of a sensing device, in accordance with an example embodiment. The transceiver 290 of FIG. 2B may form a portion of the logic 224 of FIG. 2A. The transceiver 290 may include first radio hardware 292 and second radio hardware 294. The first radio hardware 292 and second radio hardware 294 may each be configured to work with a different wireless protocol. In some examples, the first radio hardware 292 may be configured to operate based on a near-field communication (NFC) standard and/or radio frequency identification (RFID) standard and the second radio hardware 294 may be configured to operate based on a Bluetooth Low Energy (BLE) standard.

Both first radio hardware 292 and second radio hardware 294 may be coupled to an antenna for communication. In some examples, first radio hardware 292 and second radio hardware 294 may be coupled to a single antenna. In other examples, first radio hardware 292 and second radio hardware 294 may each be coupled to its own respective antenna.

As shown in FIG. 2B, first radio hardware 292 may include both a transmission module (TX) 296A and a reception module (RX) 298 that enable the first radio hardware to operate in a bidirectional communication mode. The transmission module (TX) 296A may allow first radio hardware 292 to transmit signals from an antenna based on the radio protocol of the first radio hardware 292. The reception module (RX) 298 may allow first radio hardware 292 to receive signals from an antenna based on the radio protocol of the first radio hardware 292. The second radio hardware 294 may include a transmission module 296B that enables the second radio hardware to operate in a unidirectional communication mode. The transmission module (TX) 296B may allow second radio hardware 294 to transmit signals from an antenna based on the radio protocol of the second radio hardware 294.

Thus, in the example shown in FIG. 2B, first radio hardware 292 includes both transmission and reception capabilities, whereas second radio hardware 294 includes transmission but not reception capabilities. By omitting reception capabilities, second radio hardware 294 can be made smaller and use less energy during operation. In some examples, second radio hardware 294 may not have reception capabilities due to second radio hardware 294 not having reception hardware. In other examples, the reception capabilities of second radio hardware 294 may be disabled in software.

In some examples, both the first radio hardware 292 and the second radio hardware 294 may be integrated on the same chip. In other examples, the first radio hardware 292 and the second radio hardware 294 may each be different discrete components. Additionally, the first radio hardware 292 and the second radio hardware 294 may be configured to each operate based on a different radio protocol.

Figure 3A:
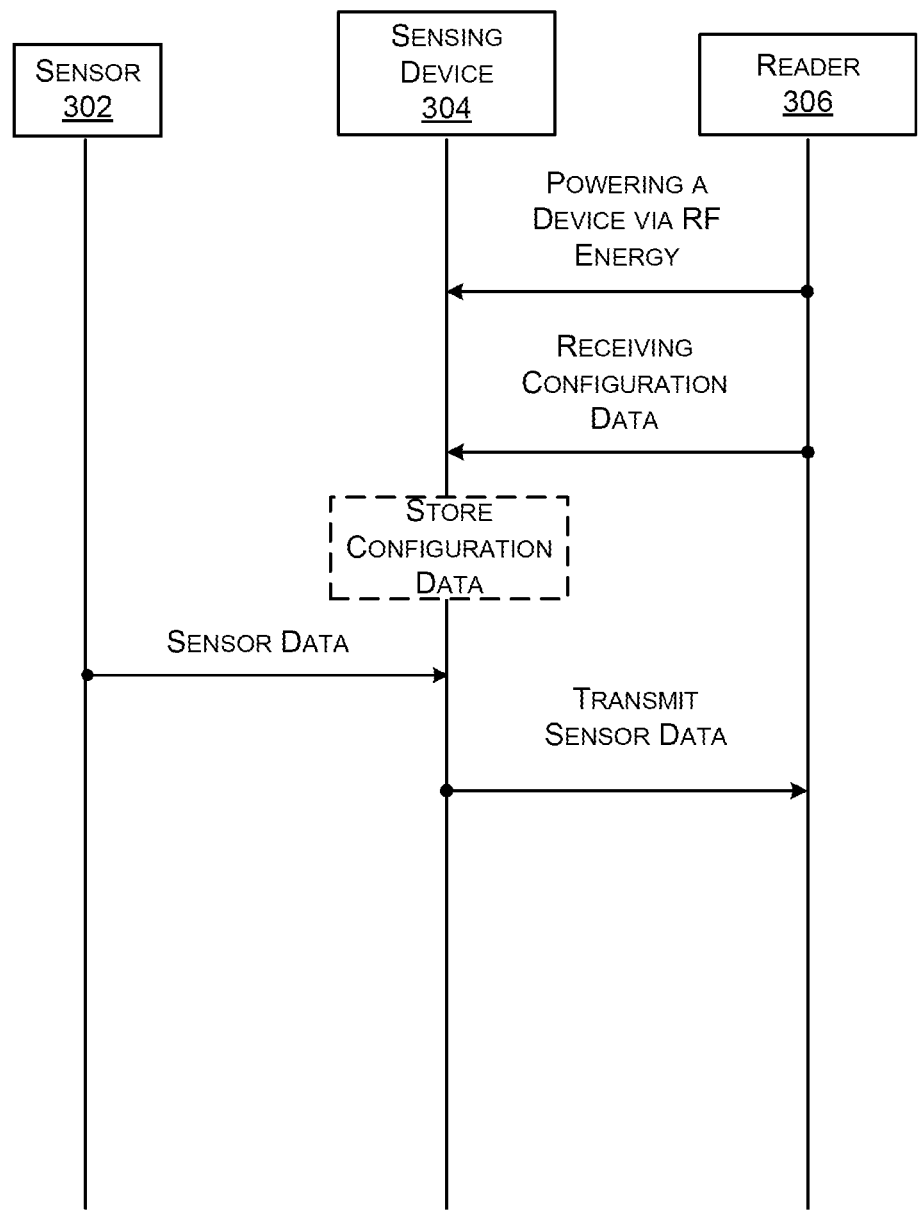
FIG. 3A is a flow diagram of a method of operation, in accordance with an example embodiment.
Figure 3B:
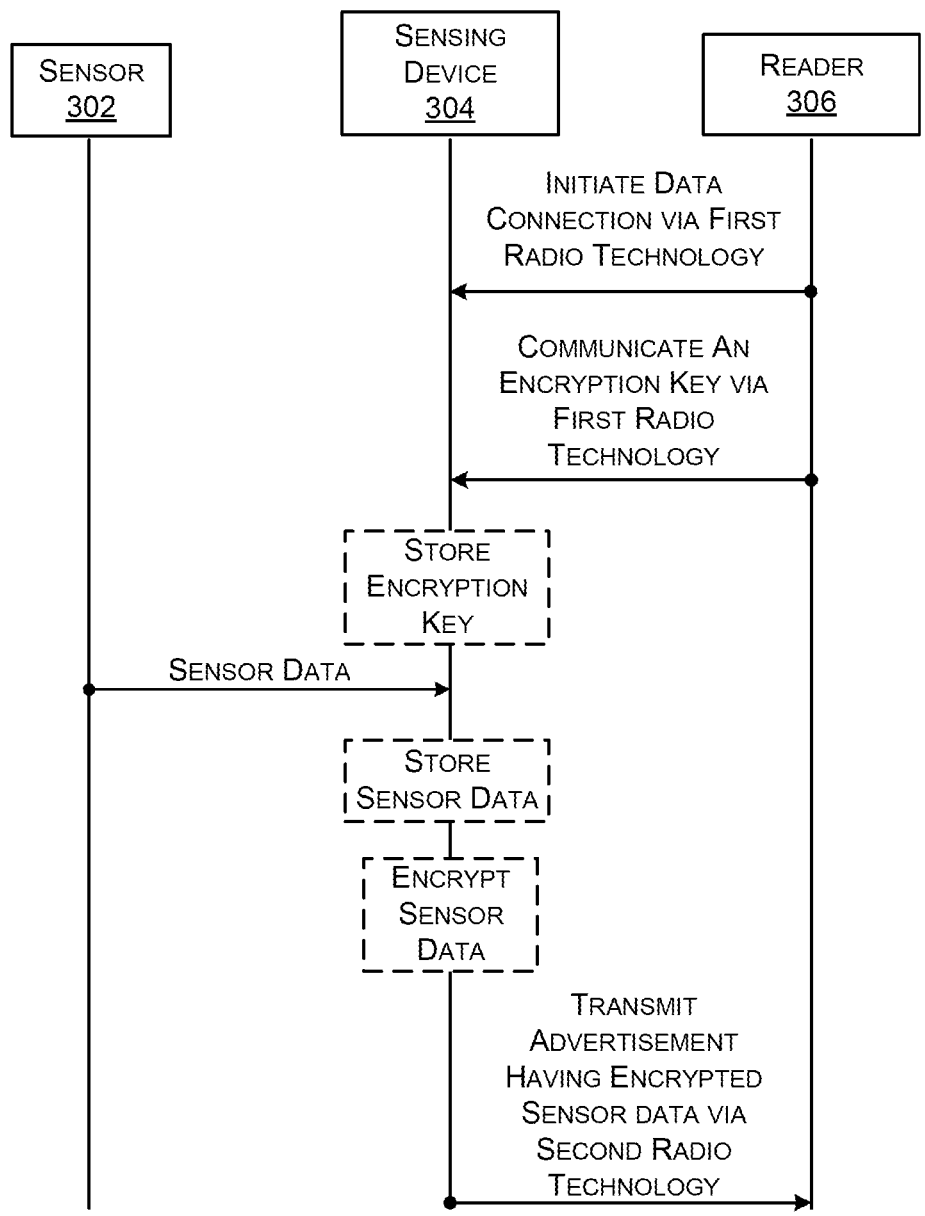
FIG. 3B is a flow diagram of a method of operation, in accordance with an example embodiment.
Figure 3C:
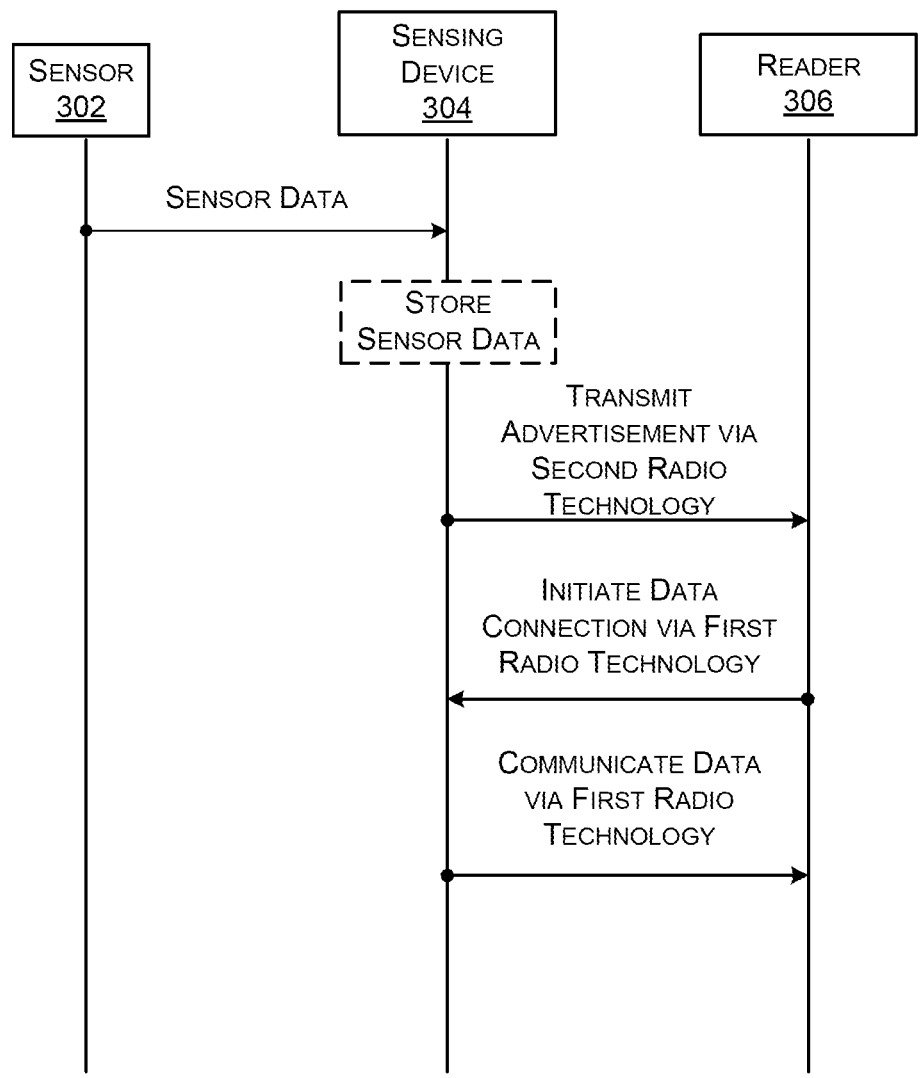
FIG. 3C is a flow diagram of a method of operation, in accordance with an example embodiment.

FIGS. 3A-3C are flow diagrams for example methods of operation of the system described herein. In these example methods, a sensing device 304 that includes a sensor 302 communicates with an external reader 306. The communication involves a first radio communication protocol used by a first radio unit of the sensing device 304 and a second radio communication protocol used by a second radio unit of the sensing device 304. In examples, the first radio communication protocol could be near field communication (NFC) protocol and the second radio communication protocol could be a Bluetooth Low Energy (BLE) protocol. It is to be understood, however, that radio communication protocols other than or in addition to NFC and BLE could be used. For example, other wireless technologies, such as Bluetooth, RFID, ZigBee (IEEE 802.15.4), IEEE 802.11-variants (such as 802.11 (b), 802.11 (g), 802.11 (n), and 802.11 (ac)), and similar wireless technologies may be used. In some examples, the first radio communication protocol may be a short-range protocol and the second radio communication protocol may be a longer range protocol. Although the three methods are shown on different figures, the various elements of the figures may be combined and the order may be changed (such as performing items in parallel). Thus, FIGS. 3A-3C should not be viewed as limiting to the three disclosed example methods.

FIG. 3A is a flow diagram of a method of operation, in accordance with an example embodiment. The method includes the reader 306 powering the sensing device 304 via radio frequency (RF) energy. As previously described, the RF energy may be received by an antenna in the sensing device and rectified into a voltage than may provide power to the sensing device 304.

The reader 306 may also provide configuration data to the sensing device 306. Both the power and the configuration data may be communicated from the reader 306 to the first radio unit of the sensing device 304 using the first radio protocol, such as an NFC protocol. The sensing device 304 may responsively store the received configuration information in a memory of the sensing device. The configuration data may include many different configuration parameters such as, but not limited to, radio communication parameters, sensing parameters, encryption parameters, calibration parameters, and power parameters. The configuration parameters may be used to configure at least one component of the sensing device 304, such as the sensor 302 and/or a processor or radio unit in the sensing device 304.

The radio communication parameters may configure the second radio unit in the sensing device 304 by including pairing information for the second radio protocol, such as a Bluetooth protocol. For example, the pairing information may allow the second radio unit of the sensing device 304 to communicate with the reader 306 via a BLE protocol. By providing radio communication parameters via the first radio protocol, the second radio protocol may function without having to perform a pairing sequence. In some instances, the second radio protocol may function without any necessary pairing. For example, the second protocol may be an 802.11-based protocol. In some 802.11 examples, data may be communicated by way of the service set identifier (SSID) of the 802.11 transmission. For example, the SSID may contain both an identification of the device causing the transmission as well as sensor data. The radio parameters may also include a timing associated with radio transmissions by the sensing device 304.

The sensing parameters may include information about how the sensing device should sample the sensor 302. Sensing parameters may include a sampling timing. The encryption parameters may include an encryption key. The encryption key may be used to encrypt data or information sent from the sensing device 304 to the reader 306. Calibration parameters may be used to communicate calibration information to the sensing device. By communicating calibration parameters, the accuracy of measurements by the sensor may be improved in situ. The power parameters may include information that enables the sensing device to operate properly with the provided power. For example, the power parameters may specify timing with the sensing device 304 may go from a sleeping state to an awake state. In the awake state, the sensing device may be able to both sample data from the sensor 302 and communicate data to the reader 306. In the sleep state, the sensing device may power off, put into a sleep state, or otherwise reduce the power usage of various components of the sensing device 306.

The sensing device 304 may receive sensor data from the sensor 302. The sensing device 304 may transmit the sensor data to the reader 306. The sensing device 304 may transmit the sensor data periodically, or at some time interval, based on the radio parameters that the reader 306 communicated to the sensing device 304. In one example, the sensor data may be transmitted by the sensing device 304 based on the second radio protocol. More specifically, the sensing device 304 may transmit a BLE advertisement packet that contains the sensor data. The reader 306 may be configured to receive BLE advertisement packets. In some examples, the sensing device 304 may encrypt the sensor data before the BLE advertisement packet is transmitted. In some further examples, the sensing device 304 may be configured to periodically transmit BLE advertisement packets based on a predetermined time interval. Thus, the sensing device 304 may be configured to transmit the sensor data without the need of a data request from the reader 306.

FIG. 3B is a flow diagram of a method of operation, in accordance with an example embodiment. In the flow diagram shown in FIG. 3B, a sensing device 304 having a sensor 302 is in communication with a reader 306. The sensing device 304 may be configured to receive and store sensor data. The sensor data may be received or sampled periodically. FIG. 3B presents a method that enables the reader 306 and the sensing device to communicate with data that has been encrypted.

The method of FIG. 3B includes the reader 306 initiating a data connection with the sensing device 304 using a first radio technology. The data connection may be a two-way information exchange between the reader 306 and the sensing device 304. For example, the data connection may be based on an NFC or RFID standard of communication. As part of the data connection, the reader 306 may also transmit power wirelessly to the sensing device 304 (as previously discussed).

Further, the reader 306 may communicate an encryption key to the sensing device 304. The sensing device 304 may use the encryption key for encrypting data stored and/or transmitted by the sensing device 304. By encrypting data, the data can only be accessed by those holding the decryption key. For example, if the sensing device 304 is a medical device, it may be desirable for the data to be encrypted so only authorized parties (e.g. those with a decryption key) may be able to decode encrypted data. When the sensing device 304 receives an encryption key, it may store the encryption key in the memory of the sensing device 304.

The sensing device 304 may also be configured to receive sensor data from a sensor 302. The sensing device 304 may receive sensor data from the sensor 302 in various ways. In some examples, the sensing device 304 may periodically sample the sensor 302 to receive sensor data. In other examples, the sensing device 304 may receive sensor data from the sensor 302 when the sensor communicates data. The sensor 302 may communicate data periodically and/or based on a change is the data captured by the sensor.

The sensing device 304 may store the sensor data from the sensor 302 in a memory of the sensing device. The sensing device 304 may also encrypt the sensor data. In some examples, the sensing device 304 may store the sensor data in an unencrypted form and encrypted the data for transmission to the reader 306. In different examples, the sensing device 304 may encrypt and store the sensor data as it is received from the sensor 302.

The sensing device 304 may also transmit an advertisement packet having encrypted sensor data via a second radio technology. For example, the sensing device 304 may be configured with a BLE transmitter and no BLE receiver. Thus the sensing device 304 may be able to operate solely as a BLE transmission device and not be capable of BLE receiving. Therefore, the sensing device 304 may be able to transmit BLE advertisement packets that include encrypted sensor data. A reader 306 may be able to receive the BLE advertisement packets without having to perform a traditional Bluetooth pairing with the sensing device 304. The reader 306 may have a decryption key with which it can decrypt the data received from the sensing device. In some other examples, the reader 306 may not include a decryption key. In these examples, the reader 306 will not be able to access the data, but may be able to communicate the encrypted data to another device that has a decryption key. In practice, the reader 306 may be used to retrieve encrypted data, such as medical information, and relay the encrypted data to a master computer system for decryption and storage. Thus, the reader does not need to have a high level of security to securely move data from the sensing device to a further computing system.

FIG. 3C is a flow diagram of a method of operation, in accordance with an example embodiment. In the flow diagram shown in FIG. 3C, a sensing device 304 having a sensor 302 is in communication with a reader 306.

As previously discussed with respect to the other examples, the sensing device 304 may be configured to receive sensor data from a sensor 302. The sensing device 304 may receive sensor data from the sensor 302 in various ways. In some examples, the sensing device 304 may periodically sample the sensor 302 to receive sensor data. In other examples, the sensing device 304 may receive sensor data from the sensor 302 when the sensor communicates data. The sensor 302 may communicate data periodically and/or based on a change is the data captured by the sensor. The sensing device 304 may store the sensor data from the sensor 302 in a memory of the sensing device.

The sensing device may transmit the sensor data periodically, or at some time interval, based on second radio parameters to the reader 306. In one example, the sensor data may be transmitted by the sensing device 304 based on the second radio protocol. More specifically, the sensing device 304 may transmit a BLE advertisement packet that contains the sensor data. The reader 306 may be configured to receive BLE advertisement packets. In some examples, the sensing device 304 may encrypt the sensor data before the BLE advertisement packet is transmitted. In some further examples, the sensing device 304 may be configured to periodically transmit BLE advertisement packets based on a predetermined time interval. Thus, the sensing device 304 may be configured to transmit the sensor data without the need of a data request from the reader 306. The advertisement may only include a small amount of data. For example, the advertisement may include only the most recent sample or measurement from the sensor 302.

The method of FIG. 3C includes the reader 306 initiating a data connection with the sensing device 304 using a first radio technology. The data connection may be a two-way information exchange between the reader 306 and the sensing device 304. For example, the data connection may be based on an NFC or RFID standard of communication. As part of the data connection, the reader 306 may also transmit power wirelessly to the sensing device 304 (as previously discussed). The sensing device 304 may responsively communicate data to the reader 306 via the first radio technology. The data communicated by the first radio technology may be a large amount of stored data (that is more than just a single measurement included in the advertisement).

In one example of the method of FIG. 3C, the sensor 302 is configured to measure a glucose level periodically, and the second radio unit of the sensing device 304 may transmit each measurement in a BLE advertisement packet. Over a period of time, the second radio unit may transmit multiple glucose measurements in multiple BLE advertisement packets. The multiple glucose measurements may also be stored in the memory of the sensing device 304 for subsequent transmission by the first radio unit of the sensing device 304. Thus, the first radio unit of the sensing device 304 may receive a request from the reader 306 and responsively transmit the multiple glucose measurements stored in the memory, the multiple glucose measurements having been previously transmitted by the second radio unit in multiple advertisement packets. Thus, the second radio unit may be configured to periodically transmit a single reading of measurement data and the first radio unit may be configured to transmit a larger amount of measurement data. In one examples, the second radio unit may transmit an advertisement packet with data from the most recent sensor reading (i.e. a near real-time sensor reading). When the reader requests data from the sensing device by way of the first radio unit, the first radio unit may be transmit all or a portion of stored measurement data. Therefore, the first radio unit may be configured to provide bulk measurement data (i.e. historical measurement data). In some examples, a sensor reading is an average or other statistical summary of individual measurements over a discrete interval of time. Sequential sensor readings can correspond to sequential intervals of time.

Figure 4:
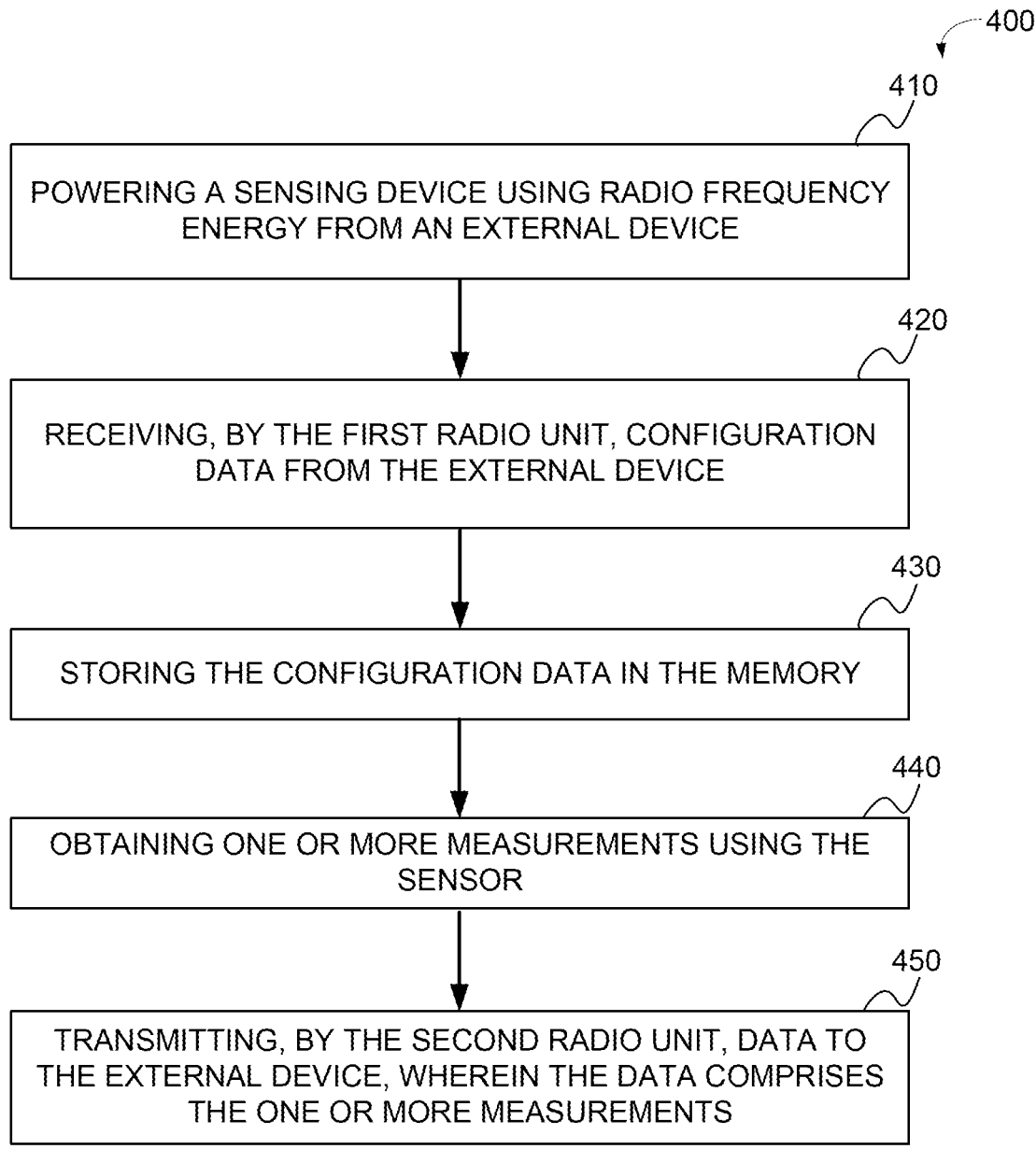
FIG. 4 is a flowchart of an example method, in accordance with an example embodiment.

FIG. 4 is a flowchart of an example method 400. Method 400 can be carried out by a device, such as a tag in a sensing device, or a device that includes a processor, such the hardware logic 224, the hardware logic may include a computer readable medium storing machine-readable instructions, where the machine-readable instructions, when executed by a processing component of the device, are configured to cause the device to carry out some or all of the techniques described herein as method 400.

Method 400 can begin at block 410. At block 410, the tag can receive electromagnetic power from an external device with an antenna, such as discussed above in the context of at least FIGS. 2A and 3A. As previously described, the electromagnetic power may be received by an antenna in the sensing device and rectified into a voltage than may provide power to the sensing device. Various components of the sensing device may use the rectified voltage as a power source.

At block 420, the sensing device may receive configuration data from the external device with a first radio unit of the sensing device. Both the electromagnetic power and the configuration data may be communicated from the external device to the sensing device with a first radio protocol of the first radio unit. As previously discussed, the first radio protocol may be an RFID protocol. The configuration data may include may different configuration parameters such as, but not limited to, radio communication parameters, sensing parameters, encryption parameters, and power parameters. The configuration data can be used to configure at least one component of the sensing device, such as a sensor, processor, and/or radio unit in the sensing device. For example, the radio communication parameters may include pairing information for a second radio protocol used by a second radio in the sensing device, such as a Bluetooth protocol. The pairing information may allow the sensing device to communicate with the external device via a Bluetooth (or semi-modified Bluetooth) protocol.

At block 430, the sensing device may responsively store the received configuration information in a memory of the sensing device.

At block 440, the sensing device may receive sensor data from the sensor. The sensor data may be stored by the sensing device in an encrypted or unencrypted format.

At block 450, the sensing device may transmit the sensor data to the external device with a second radio unit. More specifically, the sensing device may transmit a BLE advertisement packet that contains the sensor data. The external device may be configured to receive BLE advertisement packets. In some examples, the sensing device may be configured to periodically transmit BLE advertisement packets based on a predetermined time interval. Thus, the sensing device may be configured to transmit the sensor data without the need of a data request from the external device.

Figure 5:
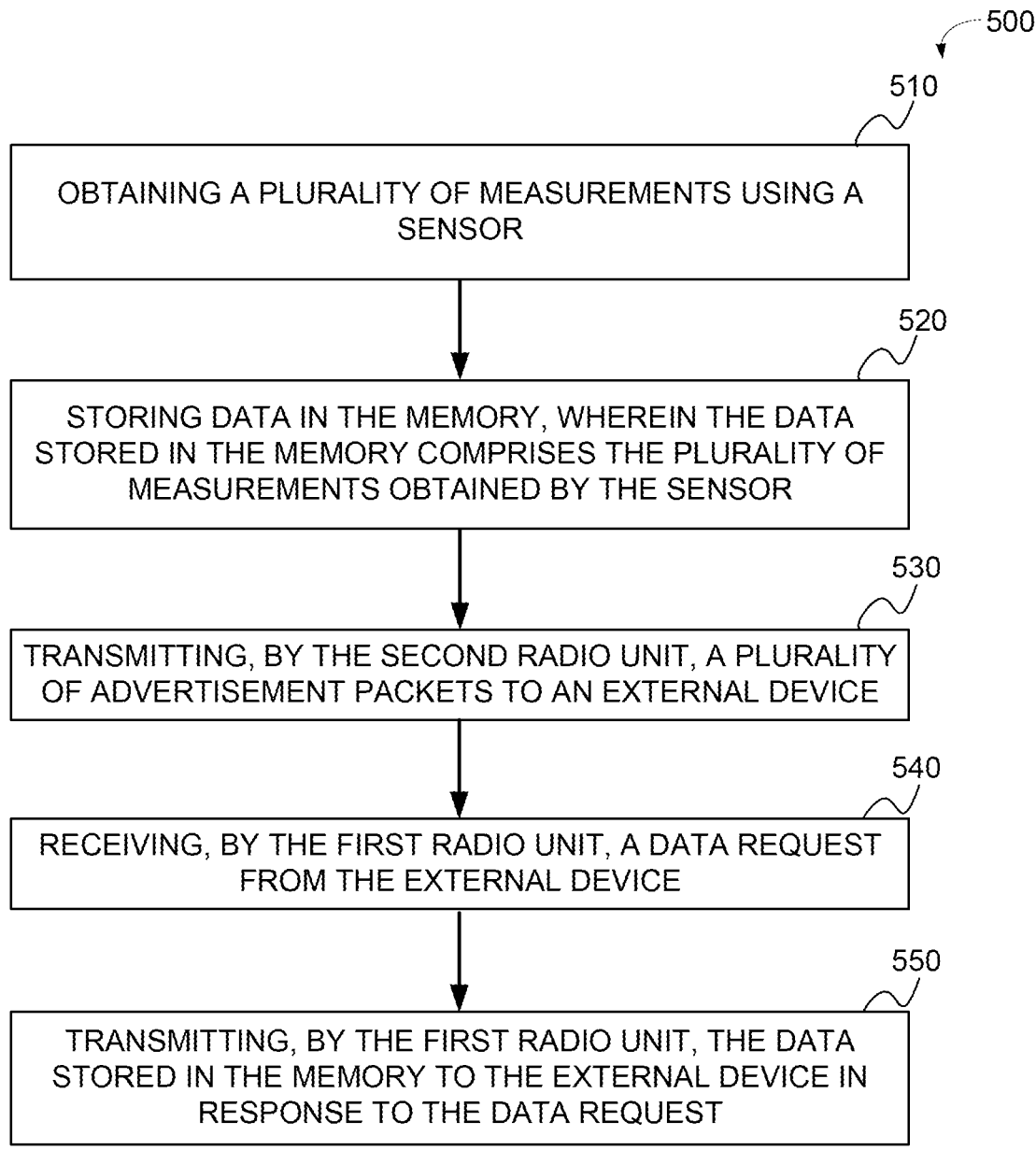
FIG. 5 is a flowchart of an example method, in accordance with an example embodiment.

FIG. 5 is a flowchart of an example method 500. Method 500 can be carried out by a device, such as a tag in a sensing device, or a device that includes a processor, such the hardware logic 224, the hardware logic may include a computer readable medium storing machine-readable instructions, where the machine-readable instructions, when executed by a processing component of the device, are configured to cause the device to carry out some or all of the techniques described herein as method 400.

Method 500 can begin at block 510. At block 510, the method includes a sensing device obtaining a plurality of measurements using a sensor of the sensing device. As previously discussed with respect to the other examples, the sensing device may be configured to receive sensor data from the sensor. The sensing device may receive sensor data from the sensor in various ways. In some examples, the sensing device may periodically sample the sensor to receive sensor data. In other examples, the sensing device may receive sensor data from the sensor when the sensor communicates data. The sensor may communicate data periodically and/or based on a change is the data captured by the sensor.

At block 520, the method includes storing data in the memory, wherein the data stored in the memory comprises the plurality of measurements obtained by the sensor. The data may be stored in either an encrypted or an unencrypted format. The memory may store the data as a plurality of time-indexed measurements from the sensor. In some examples, the memory may store the measurement values obtained from the sensor. For example, the memory may include a time-indexed set of data that includes the various measurements as each is sampled from the measurement sensor. In other examples, the memory may store summaries of the individual measurements, rather than the sensor data itself. For example, a sensor may have a range of measurements that are considered desirable. The memory may be configured to store whether or not a given measurement was in the desirable range at each time it is sampled. Additionally, the memory may also store a representation of how far a measurement was out of the desirable range (or how close it is to the edge of the desirable range) along with whether or not the measurement was in the desirable range.

At block 530, the method includes transmitting, by the second radio unit, a plurality of advertisement packets to an external device, wherein the second radio unit does not have data reception capabilities. More specifically, the sensing device may transmit a BLE advertisement packet that contains the sensor data. The external device may be configured to receive BLE advertisement packets. In some examples, the sensing device may be configured to periodically transmit BLE advertisement packets based on a predetermined time interval. Thus, the sensing device may be configured to transmit the sensor data without the need of a data request from the external device.

At block 540, the method includes receiving, by the first radio unit, a data request from the external device. The first radio unit may operate based on an NFC protocol. The external device may communicate a request for the sensing device to provide stored data to the external device. The external device may request an amount of data (such as the data from the last 24 hours) or the external device may request all the data stored by the sensing device.

At block 550, the method includes transmitting, by the first radio unit, the data stored in the memory to the external device in response to the data request. The first radio unit may transmit the data to the external device based on the NFC protocol. The data may be transmitted to the external device in either an encrypted or an unencrypted format.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

Moreover, a block that represents one or more information transmissions may correspond to information transmissions between software and/or hardware modules in the same physical device. However, other information transmissions may be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

What is claimed is:

1. A sensing device comprising:
an analyte sensor;
a memory;
a processor; and
a transceiver comprising:
a first radio unit configured for bidirectional communication with an external device using a first radio communication protocol, wherein the bidirectional communication comprises receiving configuration data from the external device; and
a second radio unit configured by the configuration data for unidirectional communication with the external device using a second radio communication protocol different from the first radio communication protocol, wherein the unidirectional communication comprises the second radio unit transmitting a second radio signal to the external device, wherein the second radio signal communicates data based on a plurality of measurements obtained by the analyte sensor; and
wherein the first radio communication protocol has a shorter range than the second radio communication protocol.

2. The sensing device of claim 1, wherein:
the configuration data comprises an encryption key;
the processor is configured to store the encryption key in the memory in response to receiving the configuration data; and
the second radio unit is configured to encrypt the data using the encryption key prior to transmitting the unidirectional communication.

3. The sensing device of claim 1, wherein:
the configuration data comprises a pairing key;
the pairing key is stored in the memory by the processor; and
the second radio unit communicates with the external device based on the pairing key.

4. The sensing device of claim 1, wherein the configuration data comprises calibration data for the analyte sensor, and wherein the processor is configured to calibrate the analyte sensor in response to receiving the configuration data.

5. The sensing device of claim 1, wherein the analyte sensor is configured to measure glucose levels in a bodily fluid.

6. The sensing device of claim 1, wherein the processor is configured to store measurements from the analyte sensor in the memory, wherein the bidirectional communication further comprises sending the measurements stored in the memory to the external device via the first radio unit, and wherein the unidirectional communication further comprises sending data based on a single measurement to the external device via the second radio unit.

7. The sensing device of claim 1, further comprising a power component configured to collect/draw radio frequency energy from the external device to supply power to the memory, the processor, the first radio unit, the second radio unit, or any combination thereof.

8. The sensing device of claim 1, wherein the first radio communication protocol is a near field communication (NFC) protocol and wherein the second radio communication protocol is a Bluetooth Low Energy (BLE) protocol.

9. The sensing device of claim 1, wherein the sensing device is a body-mountable device, a wearable device, an implantable device, or any combination thereof.

10. A method comprising:
receiving radio frequency energy from an external device by a transceiver of a sensing device, wherein the sensing device comprises:
an analyte sensor,
a memory,
a processor, and
a first radio unit configured for bidirectional communication with the external device using a first radio communication protocol, and
a second radio unit configured for unidirectional communication with the external device using a second radio communication protocol different from the first radio communication protocol, wherein the first radio communication protocol has a shorter range than the second radio communication protocol;
obtaining, by the first radio unit, configuration data from the radio frequency energy and storing the configuration data in the memory;
obtaining one or more measurements using the analyte sensor; and
transmitting, by the second radio unit, data based on the one or more measurements.

11. The method of claim 10, further comprising:
storing the one or more measurements in the memory;
receiving, by the first radio unit, an instruction from the external device; and
transmitting, by the first radio unit, the one or more stored measurements to the external device in response to the instruction.

12. The method of claim 10, wherein the configuration data comprises calibration data for the analyte sensor; and further comprising calibrating the analyte sensor based on the configuration data in response to receiving the configuration data.

13. The method of claim 10, wherein the configuration data comprises an encryption key, and wherein the data transmitted by the second radio unit is encrypted using the encryption key.

14. The method of claim 10, further comprising powering the sensing device using the radio frequency energy.

15. The method of claim 10, wherein the first radio communication protocol is a near field communication (NFC) protocol and wherein the second radio communication protocol is a Bluetooth Low Energy (BLE) protocol.

16. A sensing device comprising:
an analyte sensor configured to obtain a plurality of measurements;
a memory configured to store data related to the plurality of measurements;
a first radio unit configured for bidirectional communication with an external device using a first radio communication protocol;
a second radio unit configured for unidirectional communication using a second radio communication protocol different from the first radio communication protocol,
wherein the first radio communication protocol has a shorter range than the second radio communication protocol.

17. The sensing device of claim 16, wherein the bidirectional communication comprises a data request from the external device and communication of at least a subset of the data related to the plurality of measurements from the memory.

18. The sensing device of claim 16, wherein
the unidirectional communication comprises an advertisement packet containing data related to a most recent measurement of the plurality of measurements,
the bidirectional communication comprises a data request from the external device,
the advertisement packet is transmitted by the second radio unit before the data request is received.

19. The sensing device of claim 16, wherein the sensing device is a body-mountable device, a wearable device, an implantable device, or any combination thereof.

20. The sensing device of claim 16, wherein the first radio communication protocol is a near field communication (NFC) protocol and wherein the second radio communication protocol is a Bluetooth Low Energy (BLE) protocol.

* * * * *